United States Patent [19]

Mahieu et al.

[11] Patent Number: 5,389,362
[45] Date of Patent: Feb. 14, 1995

[54] COSMETIC COMPOSITIONS FOR THE TREATMENT OF THE HAIR AND SKIN CONTAIN POLYMER CONSTITUTED ESSENTIALLY BY REPEATING UNITS OF THE β-ALANINE TYPE

[75] Inventors: Claude Mahieu, Paris; Christos Papantoniou, Montmorency, both of France

[73] Assignee: Societe Anonyme dite: L'OREAL, Paris, France

[21] Appl. No.: 981,258

[22] Filed: Nov. 25, 1992

Related U.S. Application Data

[62] Division of Ser. No. 393,699, Jun. 30, 1982, Pat. No. 5,204,092.

[30] Foreign Application Priority Data

Jul. 3, 1981 [FR] France ................. 81 13131

[51] Int. Cl.⁶ .............. A61K 7/13; A61K 47/34; A61K 7/42
[52] U.S. Cl. ................. 424/59; 424/70.1; 424/78.03; 424/78.06; 424/78.07; 424/78.08; 424/70.6; 424/70.16; 424/70.17; 8/405
[58] Field of Search .............. 424/401, 70, 59, 71, 424/78.03, 78.06, 78.07, 78.08

[56] References Cited

U.S. PATENT DOCUMENTS

| | | |
|---|---|---|
| 2,691,643 | 10/1954 | Chirtel . |
| 2,749,331 | 6/1956 | Breslow et al. . |
| 3,927,199 | 12/1975 | Micchelli et al. . |
| 3,976,781 | 8/1976 | Kalopissis et al. . |
| 3,990,459 | 11/1976 | Papantoniou . |
| 4,030,512 | 6/1977 | Papantoniou . |
| 4,032,628 | 6/1977 | Papantoniou . |
| 4,128,634 | 12/1978 | Hase et al. . |
| 4,189,468 | 2/1980 | Vanlerberghe et al. . |
| 4,213,960 | 7/1980 | Grollier et al. . |
| 4,283,384 | 8/1981 | Jacquet et al. . |

FOREIGN PATENT DOCUMENTS

| | | |
|---|---|---|
| 2132241 | 11/1972 | France . |
| 2350834 | 5/1976 | France . |
| 2403353 | 4/1979 | France . |
| 2424292 | 11/1979 | France . |
| 2424293 | 11/1979 | France . |
| 1044363 | 11/1958 | Germany . |
| 7607314 | 1/1977 | Netherlands . |
| 2088209 | 6/1982 | United Kingdom . |

OTHER PUBLICATIONS

Kobayashi, "Poly-beta-alanine solutions for making leatherlike sheets from woolen fabrics", Chem. Abstracts, vol. 73, No. 12, Sep. 21, 1970, p. 43, 57080n.

*Primary Examiner*—Thurman K. Page
*Assistant Examiner*—Peter F. Kulkosky
*Attorney, Agent, or Firm*—Cushman Darby & Cushman

[57] ABSTRACT

A cosmetic composition comprises in solution in an appropriate vehicle at least one polymer having 50–100% of repeating units of the β-alanine type having the formula

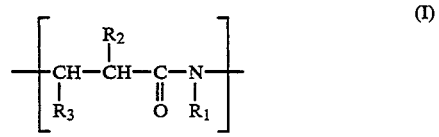

(I)

and 0–50% of repeating units of the acrylamide type having the formula

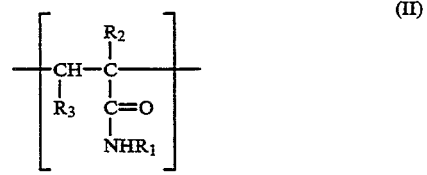

(II)

wherein $R_1$ represents hydrogen or a member selected from the group consisting of (Abstract continued on next page.)

ABSTRACT
(i) 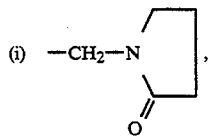,
(ii) —$CH_2OH$, (iii) —$(CH_2)_n$—$CH_3$ wherein n is 0 or a whole number from 1 to 11,
(iv) 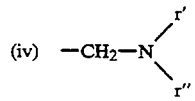
wherein r' and r" each independently represent hydrogen or alkyl having 1-3 carbon atoms, (v) —CHOH—COOH, (vi) —$CH_2$—$SO_3Na$,
(vii) 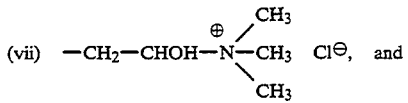, and
(viii) 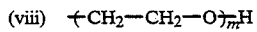
wherein m ranges from 1 to 10, and $R_2$ and $R_3$ represent hydrogen or methyl.
19 Claims, No Drawings

COSMETIC COMPOSITIONS FOR THE TREATMENT OF THE HAIR AND SKIN CONTAIN POLYMER CONSTITUTED ESSENTIALLY BY REPEATING UNITS OF THE β-ALANINE TYPE

This is a division of application Ser. No. 06/393,699, filed Jun. 30, 1982, now U.S. Pat. No. 5,204,092.

The present invention relates to a cosmetic composition for the treatment of the hair and skin containing polymers constituted by, essentially, repeating units of the β-alanine type.

Previously, there has been proposed the use, in cosmetic compositions, of polyamides of the nylon type, in the form of insoluble fine particles with the view of imparting to the compositions certain characteristics.

In particular, the use of nylon powders in emulsions imparts more fineness and unctuousness to creams containing them.

The polymers constituted essentially by repeating units of the β-alanine type, hereafter designated by the expression "polymers of the poly β-alanine type", are soluble in conventional cosmetic solvents such as water, alcohols, hydroalcoholic solutions, oils, ethyl acetate, butyl acetate and the like, and have not been the object of extensive cosmetic research.

Accordingly, to applicants' knowledge, they have never been employed in compositions for the treatment of the hair or skin.

The various tests carried out by the applicants have shown that the soluble polymers of the poly β-alanine type impart particularly desirable properties to cosmetics and thus constitute an additive of choice.

In the compositions for the hair, these polymers confer more volume (body) and hold to the hair without causing non-cosmetic phenomenon such as powdering, stickiness or a harsh appearance. In the compositions for the skin, these polymers improve the touch and render the skin more smooth and soft.

It has been noted in a surprising way that when the polymers of the poly β-alanine type are applied after a shampoo in rinse lotions or hair setting lotions, these polymers impart to the hair hold and volume, the effect of which persisted even after several shampoos.

Because of these properties in the capillary field, lotions based on these soluble polymers can then, in certain cases, be preferred to known hair setting lotions especially where one does not encounter the inherent disadvantages of these compositions, to wit, the eventual presence of a powdering effect and a certain heaviness of the hair when the relative humidity is high.

The capillary compositions according to the invention have also proved to exhibit excellent characteristics insofar as disentangling and the shininess of the hair are concerned.

When applied in the form of creams, gels or lotions the polymers of the compositions according to the invention, all impart to the skin a smooth appearance and softness to the touch and are also capable of soothing certain irritations caused by superficial cuts or sun burns. From this they find a significant use in after-shave compositions or after sun compositions.

The present invention thus relates to, as a new industrial product, a cosmetic composition for the treatment of the hair and skin, this composition containing, under a form solubilized in an appropriate cosmetic vehicle, at least one polymer having from 50 to 100% of repeating units of the β-alanine type, having the following formula:

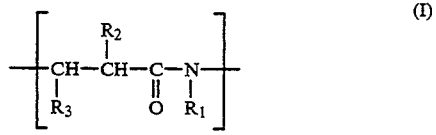

and from 0 to 50% of repeating units of the acrylamide type having the following formula:

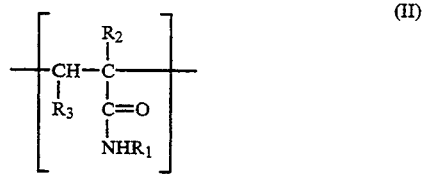

wherein $R_1$ represents hydrogen, or a member selected from the group consisting of

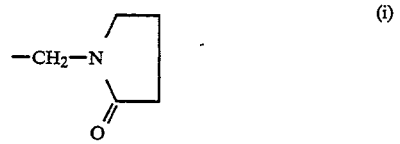

(iii) —$(CH_2)_n$—$CH_3$ wherein n is 0 or a whole number from 1 to 11,

wherein r' and r" each independently, represent hydrogen or alkyl having 1–3 carbon atoms, (v) —CHOH—COOH, (vi) —$CH_2$—$SO_3Na$,

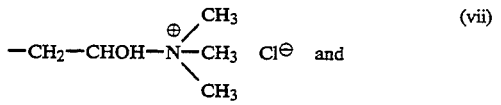

—$(CH_2$—$CH_2O)_{\overline{m}}H$     (viii)

wherein m is 1–10, and $R_2$ and $R_3$ represent hydrogen or methyl.

The soluble polymers, as defined above, are known and are obtained by anionic polymerization in an organic solvent in the presence of a base.

Representative polymers useful in the compositions according to the invention include, in particular, the poly β-alanine resulting from the polymerization of acrylamide of which the preparation has been described in U.S. Pat. Nos. 2,749,331 and 4,082,730, incorporated herein by reference.

It must be noted, however, that if, in the case of acrylamide and certain acrylamides particularly useful in the present invention, the polymerization under certain conditions, leads essentially to the formation of a polymer having the structure, corresponding to formula (I)

above, it is not always the same starting with certain N-substituted acrylamides or methacrylamides.

In effect in this case if the polymerization leads, in a more or less preponderant manner, to the formation of a polymer having a structure corresponding to formula (I), it also forms a certain percentage of a polymer having the "polyacrylamide" structure corresponding to formula II above.

Thus, starting with N-methyloxo-2-pyrrolidino acrylamide, for example, the polymerization in the presence of a base leads in part to the preponderant formation of repeating units of the N-(oxo-2 pyrrolidino N'-methyl) alanine type (A) and in part to the formation of repeating units of the acrylamido N-(oxo-2 pyrrolidino N'-methyl) type (B).

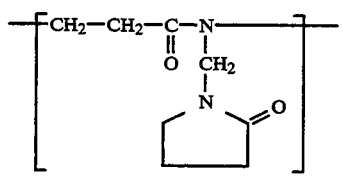
(A)

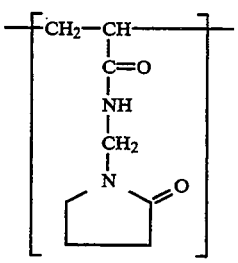
(B)

To avoid the formation of units having the acrylamide type structure of formula (II), it is possible to obtain N-substituted polymers having a structure corresponding to formula (I) by modifying the poly β-alanine by various reactions capable of introducing new functions on the nitrogen.

This process has the advantage of leading not only to completely substituted polymers but also to partially substituted polymers which can influence the desired cosmetic properties.

On the other hand, for certain values of $R_1$, it is difficult to obtain polymers constituted essentially by repeating units of formula (I) starting with N-substituted acrylamide or methacrylamide monomers, so that the process consists in modifying the poly β-alanine by means of a chemical reaction which can be indispensable in certain cases.

It should also be noted that in that which concerns the anionic polymerization of acrylamide and methacrylamide, the corresponding poly β-alanine is not only linear but can also be branched.

Finally, the importance of the terminal unit of the chains of these polymers should be noted.

In effect whatever is the next to last unit, in formula (I) or formula (II), the last unit always has the same formula:

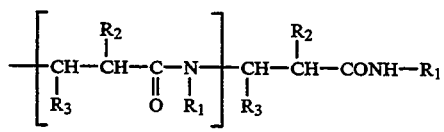
(I)

-continued

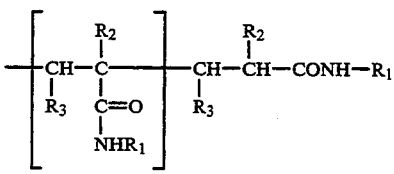
(II)

When $R_1=R_2=R_3=H$, which is the particular case of acrylamide, the polymer is nearly exclusively constituted by units of formula (I), that is to say of β-alanine units. It has been shown that subsequent reactions on poly β-alanine take place preferentially on the terminal —$CONH_2$ groups. The number of these groups is far from being negligible since in this particular case it can be between 10 and 30% of the total of the amide groups notwithstanding the relatively high molecular weight of these polymers.

This significant number of terminal —$CONH_2$ groups is due to the numerous branchings, the number of which can be regulated as a function of the polymerization process utilized.

Thus, for example, the initiation of the polymerization of acrylamide with sodium tert.butylate leads to a polymer of which the —$CONH_2$ groups represent about 17% of the total of the amide groups whereas the initiation with sodium methylate leads to a polymer of which the —$CONH_2$ groups represent 30% of the total amide groups.

Each terminal —$CONH_2$ group corresponds to one branching, hereinafter called "rate of branching" or in other words the percentage of terminal —$CONH_2$ groups relative to the total amide groups present.

In accordance with one embodiment of the invention the terminal —$CONH_2$ groups are capable of being transformed into other groups by means of various chemical reactions. Thus, the hydrolysis of the terminal —$CONH_2$ groups of poly β-alanine leads to a polymer whose terminal groups are partially or totally carboxylic acid functions.

The polymers of the compositions according to the invention can be obtained in accordance with the following two processes:

1. Preparation of a monomer corresponding to the formula:

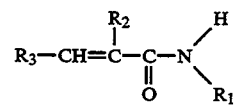

wherein:

$R_1$, $R_2$ and $R_3$ have the same meaning given above, followed by anionic polymerization in an organic solvent in the presence of a base.

2. Preparation of a poly β-alanine polymer by polymerization of acrylamide or methacrylamide in the presence of a base and subsequent reaction with the aid of a reactant capable of introducing a radical corresponding to any one of the meanings of $R_1$.

The polymers useful in the compositions according to the invention have, preferably, a molecular weight between 500 and about 200,000 and preferably between 2,000 and 100,000 (molecular weight determined according to the diffusion of light method).

As a basic polymerization catalyst there can be employed, preferably, metallic sodium, sodium hydroxide, lithium hydroxide, potassium hydroxide, sodium butylate, sodium methylate and the like, in an amount of about 0.1 to about 2 mole percent relative to the monomer.

In order to inhibit the vinyl polymerization reaction an inhibitor, such as for example N-phenyl-$\beta$-naphthylamine, can be used.

The polymerization reaction is generally carried out at a temperature in the order of 40° C. to about 140° C. and preferably between about 80° C. and about 130° C.

Representative polymerization solvents include, in particular, toluene, xylene, chlorobenzene and nitrobenzene.

The cosmetic compositions according to the invention contain the polymers, defined above, either as the principal active component or as an additive.

These cosmetic compositions can be aqueous solutions, hydroalcoholic solutions (the alcohol being principally a lower alkanol such as ethanol or isopropanol), emulsions, creams, milks or gels or they can be packaged in an aerosol containing a propellant such as nitrogen, nitrous oxide or fluorinated hydrocarbons of the "Freon" type.

Generally the concentration of the polymer in the cosmetic compositions of the present invention ranges between 0.1 and 30 percent by weight, preferably, between 1 and 10 percent by weight, based on the total weight of the composition.

In the cosmetic compositions for the hair the polymers facilitate the obtaining of a bouffant coiffure and impart to dry hair qualities of liveliness, a shiny appearance and an ease of combing.

The polymers can be present in the cosmetic compositions for the hair in accordance with the invention as an additive, or as the principal active component in hair setting lotions, hair treating compositions, hair styling lotions, hair styling creams or gels, or as an additive in shampoo compositions, hair setting compositions, permanent wave compositions, hair dyeing compositions, hair bleaching compositions, hair restructuring lotions, anti-seborrheic treating lotions or hair lacquer compositions.

The lotions are aqueous or hydroalcoholic solutions whose pH is close to neutral and can vary between about 5 and 8.

The treating creams are produced with a carrier or support based on soaps or fatty alcohols in the presence of an emulsifier. The soaps can be produced starting from natural or synthetic fatty acids having 12–20 carbon atoms, such as lauric acid, myristic acid, palmitic acid, oleic acid, ricinoleic acid, stearic acid, isostearic acid and mixtures thereof, at a concentration between 10 and 30 weight percent, and alkalizing agents, such as soda, potash, ammonia, monoethanolamine, triethanolamine and mixtures thereof.

The treating gels contain thickening agents such as sodium alginate or gum arabic or cellulose derivatives in the presence, or not, of a solvent. The concentration of the thickening agent can vary from 0.5 to 30 percent, and preferably from 0.5 to 15 percent by weight, based on the total weight of the composition.

The solvents employed can be lower aliphatic alcohols, glycols and their ethers, the concentration of these solvents ranging from 2 to 20 percent by weight, based on the total weight of the composition.

In accordance with a preferred embodiment of the invention, the compositions are provided in the form of a shampoo, characterized by the fact that it contains at least one polymer such as defined above and at least one cationic, nonionic, anionic or amphoteric detergent, or a mixture thereof.

These shampoo compositions can also contain various adjuvants such as, for example, perfumes, dyes, preservatives, thickening agents, foam stabilizers and softening agents.

In these shampoos, the detergent concentration is generally between 3 and 50 weight percent and the polymer concentration is preferably between 0.1 and 4 weight percent, based on the total weight of the composition.

The composition of the present invention can also comprise a hair setting lotion or brushing lotion, characterized by the fact that they include at least one polymer, defined above, in an aqueous or hydroalcoholic solution.

The compositions according to the invention can also be applied before or after a shampoo or even between two shampoos by acting as formulations for the treatment of hair.

They can also contain at least one cosmetic resin having anionic or cationic characteristics; the cosmetic resins used in such lotions are known and described in cosmetology literature.

The compositions according to the invention can also comprise a hair dye composition, characterized by the fact that it contains at least one polymer, defined above, at least one hair dye and a hair dye support or carrier.

The hair dye compositions are preferably gelable liquids; they contain, in addition to the polymer and the dye or dye precursor, either nonionic polyglycerolated or polyoxyethylenated derivatives, and solvents, or soaps of a liquid fatty acid such as those of isostearic or oleic acid and solvents. The soaps are soaps of soda, potash and ammonia, or of mono-, di- or triethanolamine.

The compositions according to the invention for use as a treatment for the skin are provided, preferably, in the form of creams, milks, emulsions, gels or aqueous or hydroalcoholic solutions.

The polymer concentration in these compositions can range from 0.1 to 10 percent by weight, and preferably from 0.25 to 5 percent by weight, based on the total weight of the composition.

The adjuvants generally present in these compositions are, for example, perfumes, dyes, preservatives, thickening agents, sequesterants, emulsifiers, sunscreen agents and the like.

These compositions impart to the skin an agreeable softness to the touch and render the skin smooth.

These compositions constitute, principally, creams or treating lotions for the hands or face, anti-solar creams, complexion creams, make-up remover milks, liquid bath foams, after-shave lotions, toilet water, shave foams, make-up pencils, colored or uncolored lipsticks, make-up sticks or body hygiene sticks, or even deodorant compositions.

The polymers, as defined above, can be present in compositions for treating the skin either as an additive or as the principal active component.

These compositions for the skin can also contain various active substances such as sunscreen agents, cicatrisive agents and the like, and can be provided in the form of aqueous or hydroalcoholic solutions, creams, milks and the like.

Representative sunscreen agents include "Uvinul-MS-40" sold by GAF, and Vitamin A is a representative cicatrisive agent usefully employed in the present invention.

In order to better understand the invention the following non-limiting examples of preparing the polymers as well as examples of cosmetic compositions containing them are given below.

Polymer Preparation Examples

EXAMPLE 1

In a 6 liter reactor, fitted with an agitator, a nitrogen lead-in tube and a condenser, surmounted by a calcium chloride jacket, there are introduced 0.15 g of N-phenyl β-naphthylamine and 2.5 liters of chlorobenzene. The solution is then heated to 80° C. and 150 g of acrylamide are added. After complete solution of the monomer and return of the reaction mixture to 80° C., a hot solution of 3 g of sodium previously dissolved in 300 ml of tert. butanol is added.

A polymer, insoluble in the reaction mixture, rapidly forms and is deposited on the reactor walls. The reaction is maintained for 8 hours at 80° C. At the end of the reaction the solvent is removed, before cooling, and the polymer is then dissolved in 1350 ml of water. The resulting solution is adjusted to pH 6 using concentrated HCl. The aqueous phase is washed with 500 ml of chloroform, filtered and concentrated with a rotating evaporator under reduced pressure until 350 g of oily residue are obtained. The pure polymer is obtained by slowly pouring the aqueous concentrate into 15 liters of ethanol with strong agitation, followed by filtering the suspended powder.

There are thus obtained, after drying, 135 g of white powder, for a yield of 90%.

The intrinsic viscosity of the resulting polymer, in water, at 25° C. is: $[\eta] = 0.121$ dl/g.

The spectrum of RMN-protons 250 MHz of a solution of this polymer in dimethylsulfoxide shows the presence of 98% of repeating units of formula (I) and 2% of repeating units of formula (II), wherein $R_1 = R_2 = R_3 = H$, and a branching rate of 17.5%.

EXAMPLE 2

In a 2-liter reactor, fitted with an agitator, a nitrogen lead in tube and a condenser surmounted by a calcium chloride jacket, there are introduced 0.1 g of N-phenyl β-naphthylamine, 100 g of N-methyl oxo-2 pyrrolidino acrylamide and 800 ml of chlorobenzene.

This mixture is homogenized by agitation at 50° C. and there is added a solution of 1 g of sodium in 100 ml of tert. butanol diluted with 100 ml of chlorobenzene and its temperature is adjusted to 50° C. The material is rinsed with 100 ml chlorobenzene added to the reaction mixture.

Starting from the addition of the catalyst, the solution takes on an orange color which turns toward violet. The reaction is maintained at 50° C. for 7 hours under a nitrogen atmosphere. At the end of the reaction, the reaction mixture is concentrated using a rotating evaporator under reduced pressure until 236 g of an oily residue are obtained which is then poured into 6 liters of sulfuric ether under agitation. After filtering, the recovered precipitate is redissolved in 150 ml of ethanol, the filtered solution is concentrated with a rotating evaporator under reduced pressure and again precipitated in 6 liters of sulfuric ether. The precipitate is recovered by filtration and oven dried under reduced pressure.

65 g of dry polymer are obtained having an intrinsic viscosity in water at 25° C. of: $[\eta] = 0.098$ dl/g.

The spectrum of RMN-protons 250 MHz of a solution of this polymer in dimethylsulfoxide shows the presence of 50% of repeating units of formula (I) and 50% of repeating units of formula (II) in which $R_1$ represents

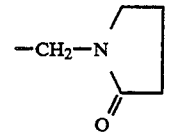

and $R_2 = R_3 = H$.

EXAMPLE 3

Into a 100 ml round bottom flask there are introduced, under a nitrogen atmosphere, 14.8 g of a 50% aqueous solution of glyoxylic acid and 8.02 g of the poly β-alanine polymer obtained in Example 1. The solution, having a pH of 1.05, is agitated with the aid of a magnetic stirrer and is heated at 40° C. for 24 hours.

The solution is purified by dialysis using a SPECTRAPOR-6 tubing, sold by Spectrum Medical Industries Inc., which eliminates simultaneously the unreacted reactants and polymers whose molecular weight is equal to or lower than 1,000. The solution is concentrated using a rotating evaporator and the polymer is precipitated with acetone. The remaining acetone solution is centrifuged, then the whole of the precipitates is dried to a constant weight at 50° C. under reduced pressure. Yield = 60%.

The spectrum of RMN-protons 250 MHz of a solution of this polymer in dimethylsulfoxide shows that 10% of the amide functions have reacted with glyoxylic acid ($R_1 = CHOH-COOH$).

EXAMPLE 4

The procedures of Example 1 are repeated using the same quantities of reactants except that 24 g of a 30% solution of sodium methylate in methanol rather than the solution of sodium tert. butylate in tert. butanol are employed.

There is thus obtained a poly β-alanine polymer whose spectrum of RMN-protons 250 MHz in dimethyl sulfoxide shows the presence of 98% of units (I) and 2% of units (II) and a rate of branching of 30%. The intrinsic viscosity of the resulting polymer is: $[\eta] = 0.086$ dl/g in solution in water at 30° C.

EXAMPLE 5

71 g of the poly β-alanine polymer prepared according to Example 1 are dissolved in 400 ml of water. There are then introduced 75 ml of a 40% commercial solution of formaldehyde and the pH is adjusted to 10.45 with 10 ml of triethylamine.

The solution is heated for 8 hours at 80° C.; then it is dialyzed using a tubing described in Example 3; concentrated using a rotating evaporator; and then poured into acetone.

The precipitated polymer is filtered, dried and characterized by RMN-protons 250 MHz in dimethyl sulfoxide, showing that 16% of the amides have undergone N-substitution by a hydroxymethyl group, ($R_1$=$CH_2OH$)

EXAMPLE 6

Preparation of a polymer resulting from the hydrolysis of the primary amide functions of the poly β-alanine polymer of Example 1.

10 g of the poly β-alanine polymer prepared according to Example 1 are dissolved in 50 ml of 4N HCl, the resulting solution is heated at 100° C. for 5 minutes. After cooling, the pH of the solution is adjusted to 10.3 with ammonia and then dialyzed in a tubing as described in Example 3. The purified solution is poured into 200 ml of ethanol and the precipitated polymer is dried and then characterized, as above. The carboxyl functions are dosed by potentiometry with 0.1N soda. Acid index=134. The spectrum RMN at $C^{13}$ of a solution of the polymer in water shows that the hydrolysis of the primary amide functions is total.

Examples of composition

EXAMPLE A

In accordance with the present invention a hair setting lotion is prepared by admixing the following components:

| Polymer of Example 1 | 3 g |
| --- | --- |
| Ethanol | 30 g |
| Water, sufficient amount for | 100 g |

This hair setting lotion when applied to hair previously washed with a shampoo imparts, after drying the hair, volume and a shiny appearance.

In this example, the polymer of example 1 can be replaced by the same amount of the polymer of Example 4.

EXAMPLE B

There is prepared, according to the present invention, a capillary lacquer by admixing the following components:

| Polymer of Example 2 | 2 g |
| --- | --- |
| Absolute ethanol | 23 g |
| Propellant mixture | |
| Freon 11 | 6.15 g  ⎫ 75 g |
| Freon 12 | 38.5 g ⎭ |

When sprayed onto the hair this lacquer imparts to the hair a good hold.

EXAMPLE C

In accordance with the present invention a body lotion is prepared by admixing the following components:

| Polymer of Example 1 or 4 | 2 g |
| --- | --- |
| Perfume | 0.2 g |
| Water, sufficient amount for | 100 g |

EXAMPLE D

There is prepared, according to the present invention, a body lotion by admixing the following components:

| Polymer of Example 2 or 4 | 1.5 g |
| --- | --- |
| Perfume | 0.1 g |
| Dye - sufficient to color the lotion | |
| Water, sufficient amount for | 100 g |

EXAMPLE E

In accordance with the present invention a hair setting lotion is prepared by admixing the following components:

| Polymer of Example 3 | 2.8 g |
| --- | --- |
| Ethanol | 35 g |
| Perfume | 0.1 g |
| Dye, sufficient to color the lotion | |
| Water, sufficient amount for | 100 g |

In this example the polymer of Example 3 can be replaced by the same amount of the polymer of Example 4 or 6.

EXAMPLE F

There is prepared, in accordance with the present invention, a lotion for the skin by admixing the following components:

| Polymer of Example 3 | 2 g |
| --- | --- |
| Perfume | 0.2 g |
| Dye, sufficient to color the lotion | |
| Water, sufficient amount for | 100 g |

EXAMPLE G

In accordance with the present invention a shampoo is prepared by admixing the following components:

| Sodium laurylether sulfate, oxyethylenated with 2.2 moles of ethylene oxide | 14 g |
| --- | --- |
| Lauric diethanolamide | 3 g |
| Polymer of Example 1 | 1 g |
| Perfume | 0.15 g |
| Dye | 0.2 g |
| Water, sufficient amount for | 100 g |

EXAMPLE H

There is prepared, according to the invention, a brushing lotion by admixing the following components:

| Polymer of Example 1 or 4 or 6 | 0.6 g |
| --- | --- |
| Trimethylcetylammonium bromide | 0.2 g |
| Perfume | 0.2 g |
| Dye | 0.4 g |
| Water, sufficient amount for | 100 g |

EXAMPLE I

In accordance with the present invention, a preshampoo composition is prepared by admixing the following components:

| Polymer of Example 2 | 1 g |
| --- | --- |
| Trimethylcetylammonium bromide | 1 g |

| Ethanol | 30 g |
|---|---|
| Water, sufficient amount for | 100 g |

EXAMPLE J

There is prepared, in accordance with the invention, a hair dye composition in the form of a cream by admixing the following components:

| Cetyl alcohol | 18 g |
|---|---|
| Ammonium lauryl sulfate (30% active material) | 12 g |
| Stearyl alcohol oxyethylenated with 15 moles of ethylene oxide | 3 g |
| Lauryl alcohol | 5 g |
| Polymer of Example 1 | 3 g |
| Ammonia - 22° Bé | 12 ml |
| Dyes | |
| m-diamino anisole sulfate | 0.048 g |
| resorcinol | 0.420 g |
| m-aminophenol | 0.150 g |
| nitro p-phenylene diamine | 0.085 g |
| p-toluene diamine | 0.004 g |
| ethylene diamine tetracetic acid | 1 g |
| sodium bisulfite d = 1.3 | 1.2 g |
| water, sufficient amount for | 100 g |

EXAMPLE K

In accordance with the present invention a sunscreen lotion is prepared by admixing the following components:

| Polymer of Example 1 or 4 | 1 g |
|---|---|
| Sunscreen agent, UVINUL-MS-40 | 3 g |
| Water, sufficient amount for | 100 g |

EXAMPLE L

There is prepared, according to the invention, a cicatrisive composition in the form of a paste by admixing the following components:

| Vitamin A | 150000 I.U. |
|---|---|
| Tyrothricine | 0.05 g |
| Polymer of Example 1 | 60 g |
| Water, sufficient amount for | 100 g |

In this example the polymer of example 1 can be replaced by the same amount of the polymer of Example 4.

EXAMPLE M

In accordance with the invention a hair restructuring lotion is prepared by admixing the following components:

| Polymer of Example 5 | 2 g |
|---|---|
| 1 N HCl solution, sufficient for pH = 2 | |
| Perfume | 0.02 g |
| Water, sufficient amount for | 100 g |

EXAMPLE N

There is prepared, according to the invention, a mascara-cream by admixing the following components:

| Triethanolamine stearate | 10 g |
|---|---|
| Candelilla wax | 15 g |
| Bees wax | 17 g |
| Xanthane gum | 1 g |
| Polymer of Example 1 | 0.5 g |
| Black iron oxide | 5 g |
| Aminosilicate polysulfide | 4 g |
| Preservatives, sufficient amount | |
| Water, sufficient amount for | 100 g |

EXAMPLE O

There is prepared, according to the invention, ampoules of a facial beauty preparation by admixing the following components:

| Polymer of Example 4 | 5 g |
|---|---|
| Glycerine | 2 g |
| Methyl p-hydroxybenzoate | 0.1 g |
| Bactericides | 0.3 g |
| Perfume | 0.2 g |
| Sterile demineralized water | 92.4 g |

EXAMPLE P

In accordance with the present invention a hydrating care cream is prepared by admixing the following components:

| Self-emulsifiable glycerol stearate | 3 g |
|---|---|
| Cetyl alcohol | 0.5 g |
| Stearyl alcohol | 0.5 g |
| Petrolatum oil | 13 g |
| Sesame oil | 10 g |
| Stearic acid | 3 g |
| Polymer of Example 1 | 2 g |
| Glycerine | 5 g |
| Methyl p-hydroxybenzoate | 0.3 g |
| Demineralized water, sufficient amount for | 100 g |

EXAMPLE Q

There is prepared, according to the invention, a beauty mask by admixing the following components:

| Polymer of Example 1 | 30 g |
|---|---|
| "Carbopol 941" sold by Goodrich Chemical Co. | 1 g |
| Triethanolamine | 1 g |
| Ethyl alcohol, 96° | 5 g |
| "Tween 20" sold by Atlas | 1.5 g |
| Perfume, sufficient amount | |
| Dye, sufficient amount to color the mask | |
| Preservatives, sufficient amount | |
| Sterile demineralized water, sufficient amount for | 100 g |

What is claimed is:

1. A hair dye composition comprising in an aqueous or hydroalcoholic solution wherein the alcohol is a lower alkanol (a) at least one polymer having 50 to 100% of repeating units of the β-alanine type having the formula

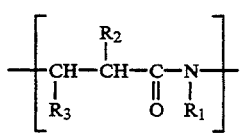 (I)

and 0 to 50% of repeating units of the acrylamide type having the formula

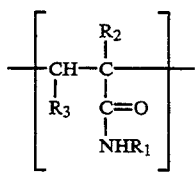 (II)

wherein
R$_1$ represents hydrogen or a member selected from the group consisting of (i) —CH$_2$—N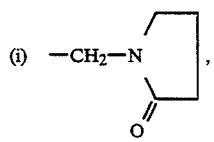, (ii) —CH$_2$OH,
(iii) —(CH$_2$)$_n$—CH$_3$ wherein n is 0 or a whole number ranging from 1 to 11, (iv) —CH$_2$—N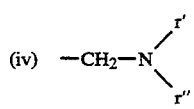

wherein r' and r" each independently, represent hydrogen or alkyl containing 1-3 carbon atoms,
(v) —CHOH—COOH,
(vi) —CH$_2$—SO$_3$Na, (vii) —CH$_2$—CHOH—N$^⊕$(CH$_3$)$_3$ Cl$^⊖$ and (viii) —(CH$_2$—CH$_2$—O)$_m$H wherein m ranges from 1 to 10, and
R$_2$ and R$_3$, each independently, represent hydrogen or methyl, said polymer being present in an amount sufficient to confer increased body and hold to the hair without causing powdering, stickiness or a harsh appearance to the hair, and
(b) a hair dye present in an amount effective to dye hair.

2. A composition for application to the skin comprising in an aqueous or hydroalcoholic solution wherein the alcohol is a lower alkanol
   (a) at least one polymer having 50 to 100% of repeating units of the β-alanine type having the formula

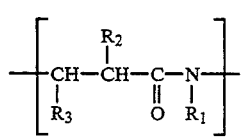 (I)

and 0 to 50% of repeating units of the acrylamide type having the formula

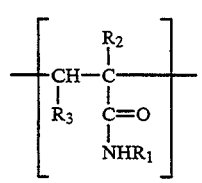 (II)

wherein
R$_1$ represents hydrogen or a member selected from the group consisting of (i) —CH$_2$—N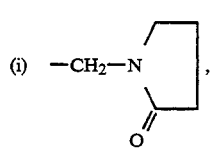, (ii) —CH$_2$OH,
(iii) —(CH$_2$)$_n$—CH$_3$ wherein n is 0 or a whole number ranging from 1 to 11, (iv) —CH$_2$—N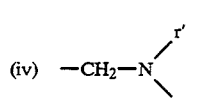

wherein r' and r" each independently, represent hydrogen or alkyl containing 1-3 carbon atoms,
(v) —CHOH—COOH,
(vi) —CH$_2$—SO$_3$Na, (vii) —CH$_2$—CHOH—N$^⊕$(CH$_3$)$_3$ Cl$^⊖$ and (viii) —(CH$_2$—CH$_2$—O)$_m$H wherein m ranges from 1 to 10, and
R$_2$ and R$_3$, each independently, represent hydrogen or methyl,
said polymer being present in an amount sufficient to soothe skin irritations and to render the skin smooth and soft, and
(b) an effective amount of a sunscreen agent.

3. A composition for application to the skin comprising in an aqueous or hydroalcoholic solution wherein the alcohol is a lower alkanol
   (a) at least one polymer having 50 to 100% of repeating units of the β-alanine type having the formula

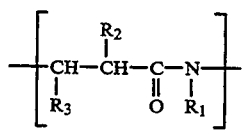

and 0 to 50% of repeating units of the acrylamide type having the formula

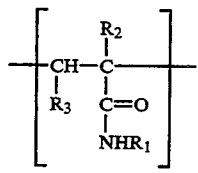

wherein
$R_1$ represents hydrogen or a member selected from the group consisting of (i) 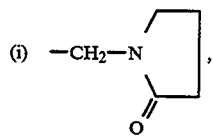

(ii) —$CH_2OH$,
(iii) —$(CH_2)_n$—$CH_3$ wherein n is 0 or a whole number ranging from 1 to 11, (iv) 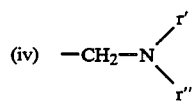

wherein r' and r" each independently, represent hydrogen or alkyl containing 1-3 carbon atoms,
(v) —CHOH—COOH,
(vi) —$CH_2$—$SO_3Na$, (vii) 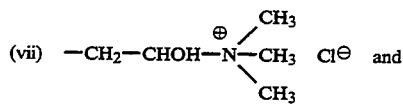 and (viii) 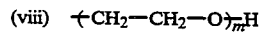

wherein m ranges from 1 to 10, and $R_2$ and $R_3$, each independently, represent hydrogen or methyl,
said polymer being present in an amount sufficient to soothe skin irritations and to render the skin smooth and soft, and
(b) an effective amount of a cicatrisive agent.

4. The hair dye composition of claim 1 wherein said polymer is present in an amount ranging from 0.1 to 30 percent by weight based on the total weight of said composition.

5. The hair dye composition of claim 1 wherein said polymer is present in an amount ranging from 1 to 10 percent by weight based on the total weight of said composition.

6. The hair dye composition of claim 1 wherein said polymer has a molecular weight ranging from 500 to 200,000.

7. The hair dye composition of claim 1 wherein said polymer has a molecular weight ranging from 2,000 to 100,000.

8. The hair composition of claim 1 wherein said polymer is poly β-alanine resulting from anionic polymerization of acrylamide.

9. The hair dye composition of claim 1 in the form of a cream, a milk, an emulsion or a gel.

10. The composition of claim 2 wherein said polymer is present in an amount ranging from 0.25 to 5 percent by weight based on the total weight of said composition.

11. The composition of claim 2 in the form of a cream, a milk, an emulsion or a gel.

12. The composition of claim 2 wherein said polymer has a molecular weight ranging from 500 to 200,000.

13. The composition of claim 2 wherein said polymer has a molecular weight ranging from 2,000 to 100,000.

14. The composition of claim 2 wherein said polymer is poly β-alanine resulting from anionic polymerization of acrylamide.

15. The composition of claim 1 wherein said polymer is present in an amount ranging from 0.25 to 5 percent by weight based on the total weight of said composition.

16. The composition of claim 1 in the form of a cream, a milk, an emulsion or a gel.

17. The composition of claim 1 wherein said polymer has a molecular weight ranging from 500 to 200,000.

18. The composition of claim 1 wherein said polymer has a molecular weight ranging from 2,000 to 100,000.

19. The composition of claim 1 wherein said polymer is poly β-alanine resulting from anionic polymerization of acrylamide.

* * * * *